(12) United States Patent
Courchesne

(10) Patent No.: US 6,221,903 B1
(45) Date of Patent: Apr. 24, 2001

(54) AMIODARONE AS AN ANTIFUNGAL AGENT

(75) Inventor: William E. Courchesne, Soda Springs, CA (US)

(73) Assignee: University and College of Nevada, Reno, Reno, NV (US)

( * ) Notice: Subject to any disclaimer, the term of this patent is extended or adjusted under 35 U.S.C. 154(b) by 0 days.

(21) Appl. No.: 09/480,381

(22) Filed: Jan. 10, 2000

Related U.S. Application Data

(60) Provisional application No. 60/115,423, filed on Jan. 11, 1999.

(51) Int. Cl.⁷ .................................................. A61K 31/343
(52) U.S. Cl. ............................................................ 514/469
(58) Field of Search ............................................. 514/469

(56) References Cited

PUBLICATIONS

The Merck Index (12th edition), p. 84, 1996.*

\* cited by examiner

*Primary Examiner*—Phyllis G. Spivack
(74) *Attorney, Agent, or Firm*—Ian F. Burns

(57) ABSTRACT

The present invention relates to methods of treating fungal infections and methods of killing or inhibiting growth of fungi with an amiodarone compound.

11 Claims, 5 Drawing Sheets

FIG.1A,B. CELLS WERE GROWN OVERNIGHT IN SD AT 30°C TO DENSITIES OF ABOUT 7-21 X 10⁶ CELLS/ML. ALIQUOTS WERE ADDED TO FRESH SD MEDIA CONTAINING DMSO ONLY OR VARIOUS CONCENTRATIONS OF AMIODARONE IN DMSO. CULTURES WERE INCUBATED AT 30°C AND CELL DENSITIES WERE MONITORED SPECTROPHOTOMETRICALLY. (A) AND (B): EXPERIMENTS 1 AND 2.

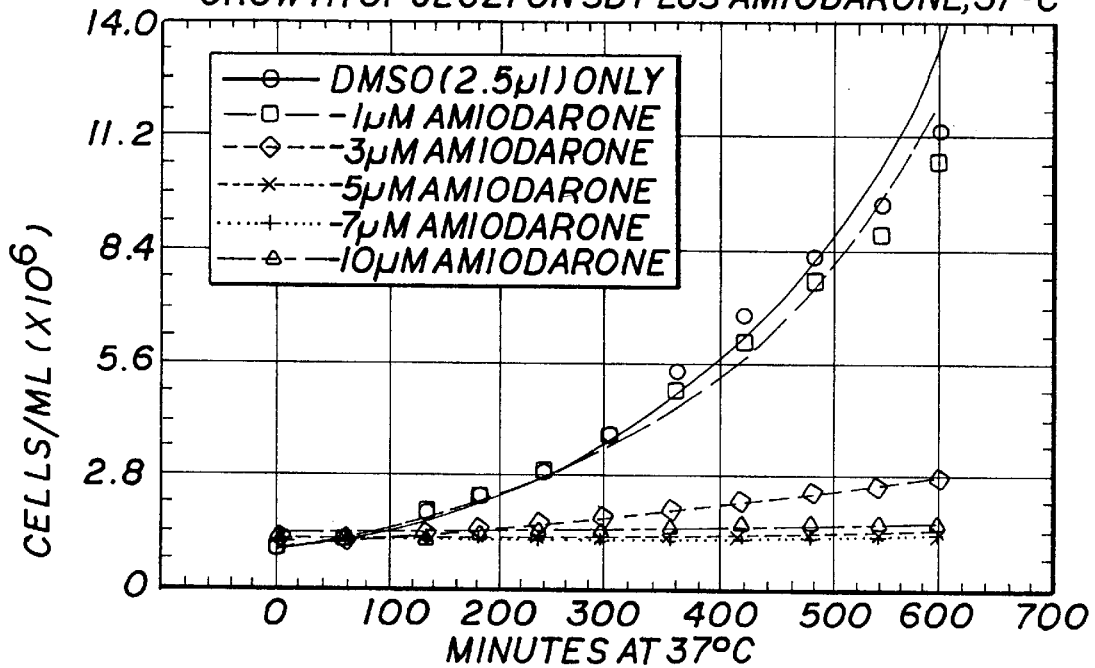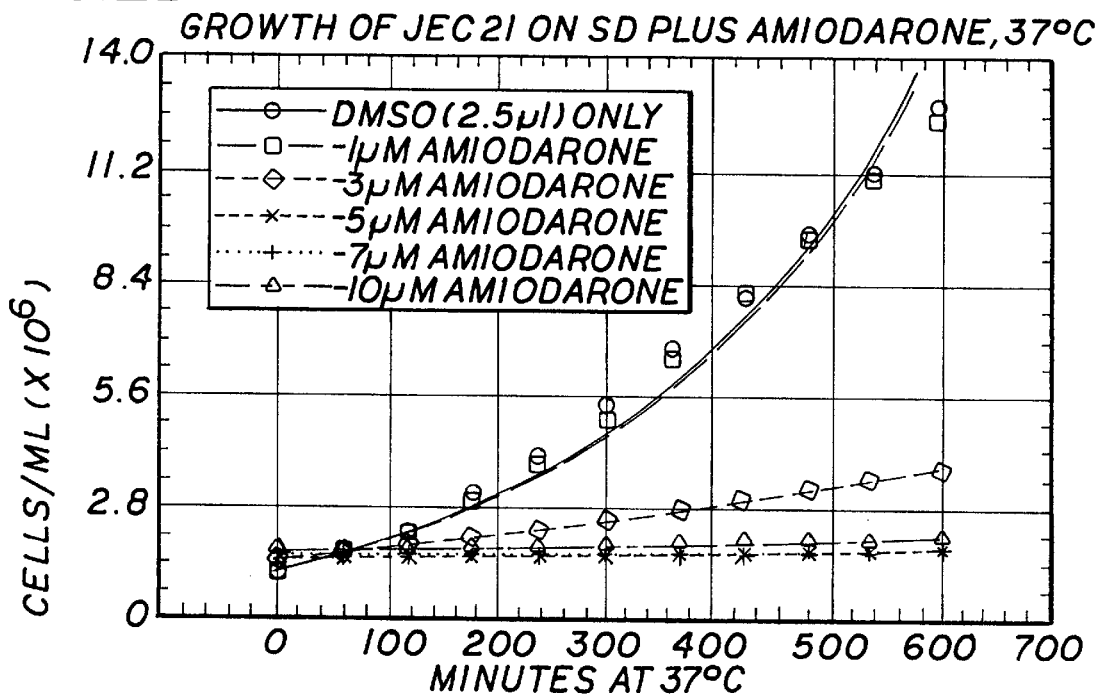
FIG.2A,B CONDITIONS WERE IDENTICAL TO THOSE IN FIG.1A,B EXCEPT THAT GROWTH WAS MONITORED AT 37°C. (A) AND (B): EXPERIMENTS 1 AND 2.

FIG. 3A
GROWTH OF CRYPTOCOCCAL CELLS PLUS AMIODARONE (30°C)

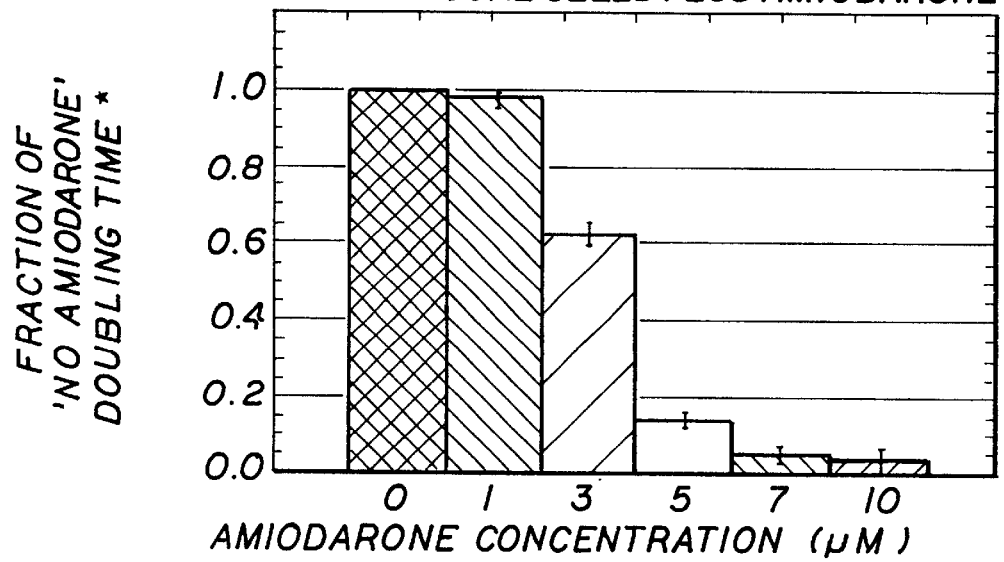

FIG. 3B
GROWTH OF CRYPTOCOCCAL CELLS PLUS AMIODARONE (37°C)

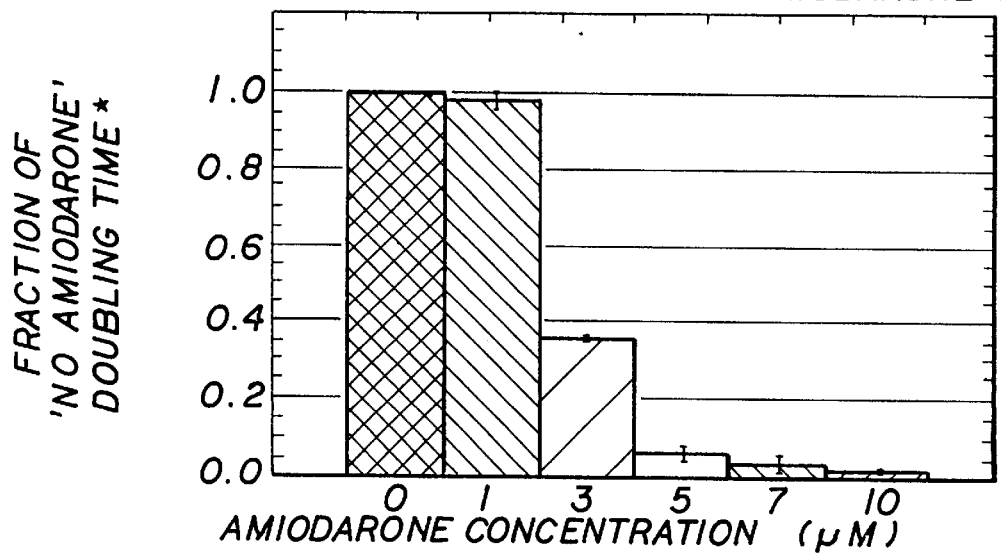

FIG. 3A,B. DOUBLING TIMES WERE CALCULATED FROM THE GROWTH CURVES SHOWN IN FIG. 1A,B AND 2A,B. THESE VALUES ARE PRESENTED AS THE RATIO OF THE DOUBLING TIME OF JEC21 CELLS IN THE ABSENCE OF AMIODARONE VERSUS THE DOUBLING TIME IN THE PRESENCE OF THE INDICATED CONCENTRATION OF AMIODARONE. SMALLER RATIOS INDICATE SLOWER GROWTH RATES FOR CELLS CONTAINING AMIODARONE. STANDARD ERROR BARS ARE SHOWN FIG. 3A AND 3B ARE THE RATIOS FOR CELLS INCUBATED AT 30°C AND 37°C RESPECTIVELY.

FIG.4A,B GROWTH-RESPONSE CURVES OF C.NEOFORMANS STRAINS 271 AND J9D IN THE PRESENCE OF AMIODARONE WERE DETERMINED. CONDITIONS WERE IDENTICAL TO THOSE IN FIG.1A AND B: RESPONSES FOR STRAINS 271 AND J9D, RESPECTIVELY.

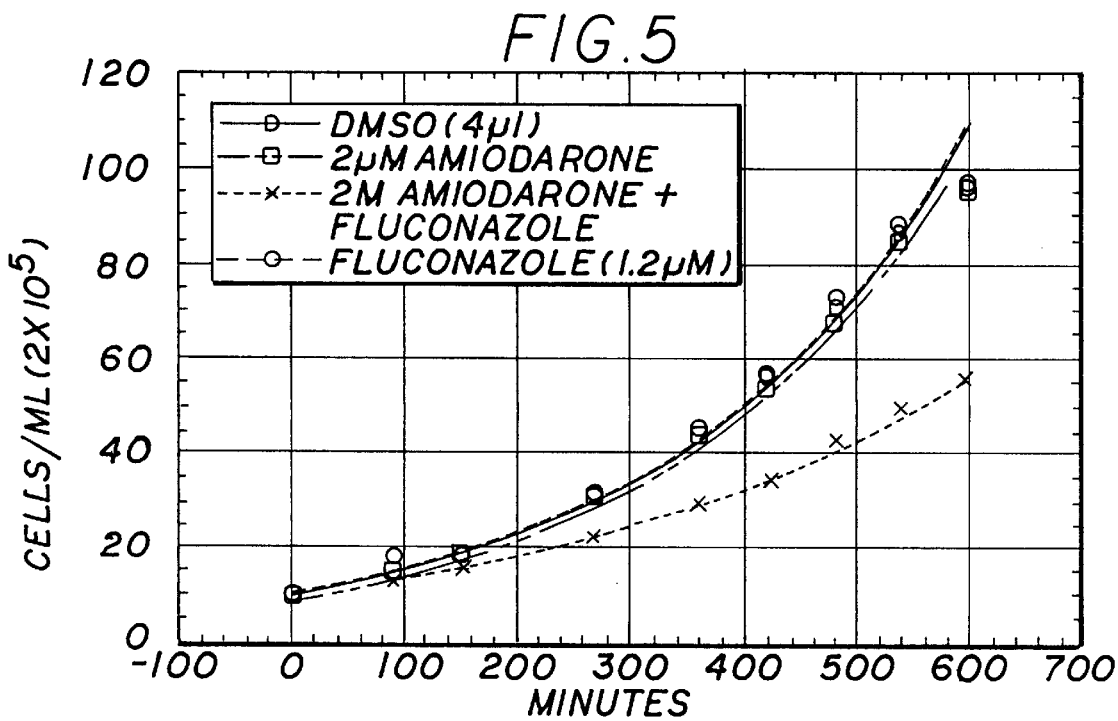
FIG. 5. GROWTH-RESPONSE CURVES OF C. NEOFORMANS STRAIN JEC21 IN PRESENCE OF AMIODARONE (2μM), FLUCONAZOLE (1.2μM), OR A COMBINATION OF THESE TWO DRUGS.
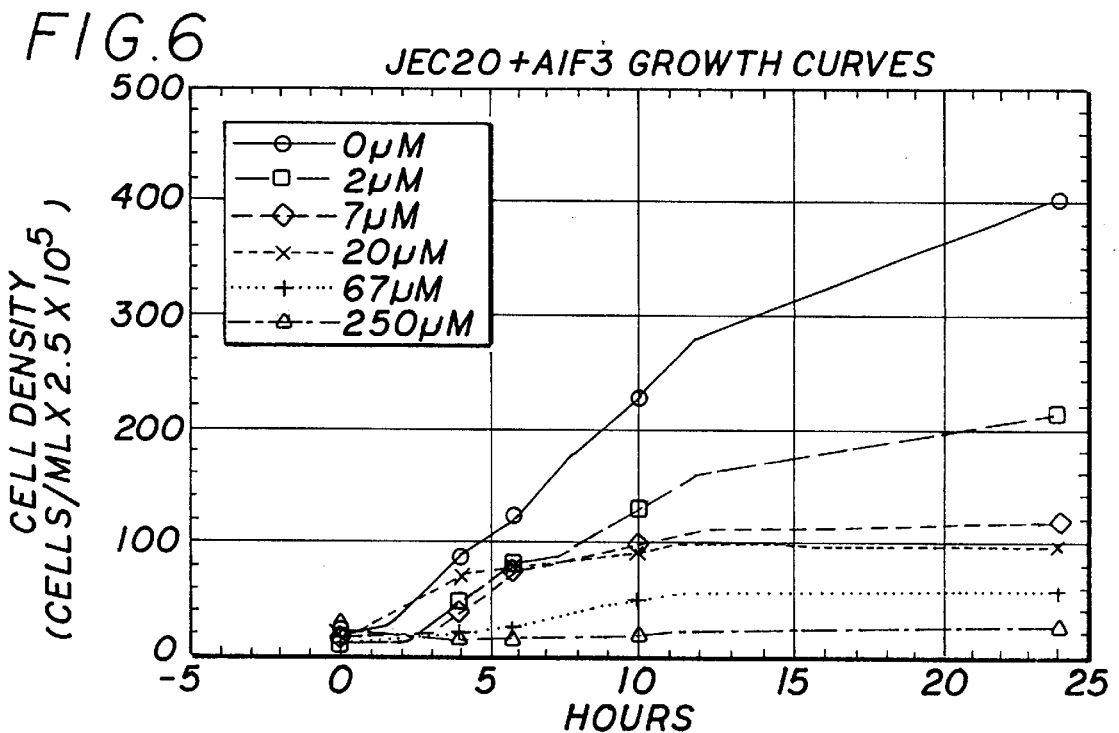
FIG. 6. JEC20 CELLS WERE GROWN IN SD MEDIUM OVERNIGHT. CELLS WERE DILUTED INTO FRESH GROWTH MEDIUM CONTAINING THE INDICATED CONCENTRATIONS OF ALUMINUM FLOURIDE AND CELL DENSITY WAS MONITORED.

AMIODARONE AS AN ANTIFUNGAL AGENT

This application claims the benefit of U.S. application Ser. No. 60/115,423 filed Jan. 11, 1999, which application is hereby incorporated by reference in its entirety.

FIELD OF THE INVENTION

The present invention relates generally to methods of treating fungal infections and methods of killing or inhibiting growth of fungi with an amiodarone compound.

BACKGROUND OF THE INVENTION

Overview

Pathogenic fungi occur world wide and are major agricultural and health pests. Fungal infections in humans range from superficial and cutaneous to deeply invasive and disseminated. Treatment of fungal infections has lagged behind bacterial chemotherapy. There are substantially fewer antifungal drugs than antibacterial drugs.

In the last two decades, nearly 12 million people have died of acquired immunodeficiency syndrome (AIDS) after being infected with HIV, the human-immunodeficiency virus. AIDS is defined by the occurence of at least one of more than two dozen opportunistic infections. Fungal opportunistic infections such as candidiasis, cryptococcosis, and histoplasmosis, occur frequently in patients with AIDS. Among the opportunistic infections, fungal infections caused by Pneumocystis, Candida, Cryptococcus, or Histoplasma were the first to occur in more than 50% of persons with AIDS; and at time of death, nearly 85% of decedents had a fungal infection (Jones, et al., 1999, MMWR 48: 1–22).

*Cryptococcus neoformans* is an opportunistic yeast pathogen that infects individuals with a compromised immune system, such as those with AIDS or those undergoing cancer chemotherapy (Kwon-Chung and Bennett, 1992, in *Medical Mycology*, pp. 397–446; Mitchell and Perfect, 1995, *Clin. Microbiol. Rev.* 8: 515–548; Sugar, 1991, *Mycopathologia* 114: 153–157). Its normal habitat is worldwide in pigeon droppings, and one variety is associated with eucalyptus trees (Ellis and Pfeiffer, 1992, *Eur. J. Epidemiol.* 8: 321–325; Levitz, 1991, *Reviews of Infect. Dis.* 13: 1163–1169; Pfeiffer and Ellis, 1991, *J. Infect. Dis.* 163: 929–930). The most common infection caused by this yeast is a lethal meningitis (Chuck and Sande, 1989, *N. Engl. J. Med.* 321: 794–799; Kovacs, et al., 1985, *Ann. Intern. Med.* 103: 533–538; Rozenbaum, et al., 1994, *Clin. Infect. Dis.* 18: 369–380; Stanseld, 1993, *Semin. Respir. Infect.* 8: 116–123; Zuger, et al., 1986, *Ann. Intern. Med.* 104: 234–240). Infection with *C. neoformans* begins with inhalation of infectious particles, and is first established in the lungs. Cryptococcosis is one of the defining diseases associated with AIDS, and nearly 10% of all AIDS patients have cryptococcosis.

Treatments for fungal infections include azole antifungal drugs, such as clotrimazole, ketaconazole, fluconazole, and itraconazole (for a review, see Graybill, 1996, *Clin. Infect. Dis.* 22: S166-S178). The azoles act by inhibiting an enzyme, lanosterol demethylase, that participates in the synthesis of ergosterol, an essential component of fungal membranes. Other commonly used drugs include flucytosine and amphotericin B. Amphotericin B is one of the most effective antifungal drugs but must be given intravenously and causes serious side effects. Resistance to antifungals has become more apparent in recent years and may worsen with the increase in prophylatic therapy.

There is intense interest in identifying new drugs with different modes of action against fungal infections. The current repertoire of antifungals has limitations such as insufficient efficacy, the need for intravenous administration, serious side effects, or the appearance of resistant fungal strains. Importantly, most of the current treatments are fungistatic, that is, they inhibit fungal growth but do not cause outright death. Subsequent clearing of these inhibited fungi is inadequate in patients with defective immune systems. Thus, it is imperative to identify fungicidal agents and, if possible, their cellular targets that, when impaired, lead to fungal cell death.

Fungi and Antifungal Agents

Fungi are eukaryotic cells that may reproduce sexually or asexually and may be biphasic, with one form in nature and a different form in the infected host. Fungal diseases are referred to as mycoses. Some mycoses are endemic, i.e. infection is acquired in the geographic area that is the natural habitat of that fungus. These endemic mycoses are usually self-limited and minimally symptomatic. Some mycoses are chiefly opportunistic, occurring in immunocompromised patients such as organ transplant patients, cancer patients undergoing chemotherapy, burn patients, AIDS patients, or patients with diabetic ketoacidosis.

Fungal infections are becoming a major health concern for a number of reasons, including the limited number of antifungal agents available, the increasing incidence of species resistant to older antifungal agents, and the growing population of immunocompromised patients at risk for opportunistic fungal infections. The incidence of systemic fungal infections increased 600% in teaching hospitals and 220% in non-teaching hospitals during the 1980's. The most common clinical isolate is *Candida albicans* (comprising about 19% of all isolates). In one study, nearly 40% of all deaths from hospital-acquired infections were due to fungi. (Sternberg, 1994, *Science* 266: 1632–1634).

Neutropenic patients (due to, e.g., chemotherapy, immunosuppressive therapy, infection, including AIDS, or an otherwise dysfunctional immune system) are predisposed to the development of invasive fungal infections, most commonly including Candida species and Aspergillus species, and, on occasion, Fusarium, Trichosporon and Dreschlera. Cryptoccocus infection is also common in patients on immunosuppressive agents.

The majority of known antifungal agents fall into one of three main groups. The major group includes polyene derivatives, including amphotericin B and the structurally related compounds nystatin and pimaricin, which are only administered intravenously. These are broad-spectrum antifungals that bind to ergosterol, a component of fungal cell membranes, and thereby disrupt the membranes, leading to cell death. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of antifungal agents includes azole derivatives which impair synthesis of ergosterol and lead to accumulation of metabolites that disrupt the function of fungal membrane-bound enzyme systems (e.g., cytochrome P450) and inhibit fungal growth. Significant inhibition of mammalian P450 results in important drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole and is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of antifungal agents includes allylamnines-thiocarbamates, which are generally used to treat skin infections. This group includes tolnaftate and naftifine.

Another antifungal agent is griseoflulvin, a fungistatic agent which is administered orally for fungal infections of skin, hair or nails that do not respond to topical treatment.

Most endemic mycoses are acquired by the respiratory route and are minimally symptomatic; cough, fever, headache, and pleuritic pain may be seen. Occasionally, endemic mycoses may cause progressive pulmonary disease or systemic infection. Histoplasmosis, caused by Histoplasma, is the most common endemic respiratory mycosis in the United States; over 40 million people have been infected. The disease is noncontagious and ordinarily self-limited, but chronic pulmonary infection and disseminated infection may occur. Pulmonary infection rarely requires treatment, but disseminated infection may be treated with amphotericin B. Coccidioidomycosis, caused by Coccidioides, is a noncontagious respiratory mycosis prevalent in the southwest United States. It also is usually self-limited but may lead to chronic pulmonary infection or disseminated infection. Amphotericin B or miconazole may be given for treatment. Blastomycosis, caused by Blastomyces is a noncontagious, subacute or chronic endemic mycosis most commonly seen in the southeast United States. Most pulmonary infections are probably self-limited. Patients with progressive lung disease or disseminated disease, and immunocompromised patients, may be treated systemically with amphotericin B. Paracoccidioidomycosis, caused by Paracoccidioides, is a noncontagious respiratory mycosis that is the most common systemic mycosis in South America. It may be acute and self-limited or may produce progressive pulmonary disease or extrapulmonary dissemination. Disseminated disease is generally fatal in the absence of therapy. Sulfonamides may be used but have a low success rate. Amphotericin B produces a higher response rate but relapses may still occur.

Cryptococcosis is a noncontagious, often opportunistic mycosis. It is characterized by respiratory involvement or hematogenous dissemination, often with meningitis. A major etiologic agent is *C. neoformans*. Most pulmonary infections are probably overlooked, but cryptococcal meningitis, which accounts for 90% of reported disease, is dramatic and seldom overlooked. Cryptococcosis is a particular problem in immunocompromised patients; cryptococcal meningitis occurs in 7 to 10% of AIDS patients. The principal symptom of meningitis is headache; associated findings include mental changes, ocular symptoms, hearing deficits, nausea, vomiting, and seizures. Without treatment, 80% of patients die within two years. In meningitis, cryptococci can be observed in India ink preparations of cerebrospinal fluid sediment, and can be cultured from the cerebrospinal fluid. Treatment is generally with fluconazole or the combination of amphotericin B and flucytosine, although amphotericin B does not cross the blood brain barrier.

Aspergillosis is a term that encompasses a variety of disease processes caused by Aspergillus species. Aspergillus species are ubiquitous; their spores are constantly being inhaled. Of the more than 300 species known, only a few are ordinarily pathogenic for man: *A. fumigatus, A. flavus, A. niger, A. nidulans, A. terreus, A. sydowi, A. flavatus*, and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of cases, there is hematogenous spread to other sites. Aspergillosis is also a rare but devastating complication of burn wounds; amputation is often required for cure. Invasive aspergillosis is commonly fatal, so aggressive diagnosis and treatment is required. Blood, urine and cerebrospinal fluid cultures are rarely positive, but fungi can be seen in smears and biopsies. Amphotericin B can be given for treatment.

Dermatophytosis is a chronic fungal infection of the skin, hair or nails by dermatophytes, which include members of the species Trichophyton, Microsporum and Epidermophyton. Infection of the foot (tinea pedis), scalp (tinea capitis) are most common, although widespread infection on non-hair-bearing skin (tinea corporis) also occurs. Clinical manifestations vary and may present on the skin as fissuring or lesions with scaling, vesicles or pustules (and alopecia on the scalp), or on the nails as discolored or chalky, crumbling nails. Both topical and systemic therapies may be used to treat dermatophyte infection, including topically administered imidazoles and triazoles (such as itraconazole, miconazole, ketoconzaole and econazole), haloprogin, undecylic acid, ciclopirox olamine, tolnaftate and terbinafine.

Fusarium species can cause localized or hematogenously disseminated infection (fusariosis), most frequently in patients who have a hemopoietic malignancy and neutropenia. Abrupt onset of fever, sometimes with myalgia, is followed in the majority of cases by distinctive skin lesions resembling ecthyrna gangrenosum. Infection can be treated with amphotericin B but recovery depends ultimately on alleviation of neutropenia. Mortality typically exceeds 90%.

Mucormycosis is an acute suppurative opportunistic mycosis that produces rhinocerebral, pulmonary or disseminated disease in immuno-compromised patients, and local or disseminated disease in patients with burns or open wounds. Infection is caused by fungi in the class Zygomycetes, and include Basidiobolus, Conidiobolus, Rhizopus, Mucor, Absidia, Mortierella, Cunninghamella, and Saksenaea Rhinocerebral mucormycosis accounts for about half of all cases of mucormycosis. It is one of the most rapidly fatal fungal diseases, with death occurring within 2–10 days in untreated patients. Early clinical signs include nasal stuffiness, bloody nasal discharge, facial swelling and facial pain. The infection then spreads to the eyes, cranial nerves and brain. Pulmonary mucormycosis is nearly as common as rhinocerebral disease and manifests with the same necrotizing and infarction as aspergillosis. Fungi are virtually never seen or cultured from blood, sputum or cerebrospinal fluid. Disseminated mucormycosis may follow pulmonary or burn wound infection. Treatment is with amphotericin B.

Candidiasis is a general term for a variety of local and systemic processes caused by colonization or infection of the host by species of the yeast Candida. Candidiasis occurs worldwide; superficial infections of the skin, mouth and other mucus membranes are universal. Invasive systemic disease has become a problem due to the use of high doses of antibiotics that destroy normal bacterial flora, immunosuppressive agents, and agents toxic to bone marrow, e.g., during cancer therapy. Neutropenia is a major risk factor for Candida dissemination. Candidiasis is also seen among immunocompromised individuals such as AIDS patients, organ transplant patients, patients receiving parenteral nutrition, and cancer patients undergoing radiation treatment and chemotherapy. It is the most common opportunistic mycosis in the world. The most common etiologic agent is *Candida albicans*. Other infectious species include *C. tropicalis, C. parapsilosis, C. stellatoidea, C. kusei, C. parakwsei, C. lusitaniae, C. pseudotropicalis, C. guilliermondi* and *C. glabrata*. *Candida albicans* is normally found in the mouth, throat, gastrointestinal tract and vagina of humans. Non-albicans species frequently colonize skin. Candida species occur in two forms that are not temperature- or host-dependent. The usual colonizing forms are yeasts that may assume a pseudomycelial configuration, especially during tissue invasion. Pseudomyceliae result from the sequential budding of yeasts into branching chains of elongated organisms.

*Candida albicans* contains cell wall mannoproteins that appear to be responsible for attachment of the yeast cells to specific host tissues. It has been reported that the mannan portion, rather than the protein portion, of the mannoproteins is responsible for adherence of finmgal cells to spleen and lymph node tissues in mice. (Kanbe, et al., 1993, *Infection Immunity* 61: 2578–2584).

*C. albicans* also binds avidly to extracellular matrix (ECM) proteins such as fibronectin, laminin, and types I and IV collagen, all of which contain heparin-binding domains. This suggests *C. albicans* may express a heparin-like surface molecule. Adherence of *C. albicans* to the ECM may be important in the pathogenesis of disseminated candidiasis. It has been demonstrated that heparin, heparan sulfate and dextran sulfate glycosaminoglycans (GAGs) inhibit adherence of *C. albicans* to ECM and ECM proteins, possibly by a mechanism involving binding of GAGs to ECM proteins, thus masking these selective ligands. (Klotz, et al, 1992, *FEMS Microbiology Letters* 78: 205–208).

Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy to gray pseudomembrane that covers the tongue, mouth, or other oropharyngeal surfaces and may be accompanied by ulceration and necrosis. Laryngeal involvement results in hoarseness. Esophagitis is often an extension of oropharyngeal disease and may manifest with symptoms of retrosternal pain and dysphagia. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial Candida infection of the skin, scalp, nails and mucus membranes.

Most cases of systemic candidiasis are caused by *Candida albicans* and *C. tropicalis*, and increasingly, *C. glabrata*. Clinical manifestations of Candida infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic Candida infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid. Involvement of the lungs is also common, but pulmonary lesions are usually too small to be seen on chest X-ray. Finally, Candida endocarditis can occur in patients receiving prolonged intravenous therapy or cardiac valve implants, or in intravenous drug abusers. Fungal lesions appear on the valves, and can embolize and occlude large blood vessels.

Superficial infections are diagnosed by microscopic examination of scrapings or swabs of infected lesions in the presence of 10% potassium hydroxide. Candida organisms can also be seen on gram stain. Endocarditis is diagnosed by blood cultures or demonstration of bulky valvular lesions on echocardiography. Systemic candidiasis may be difficult to diagnose because the presence of heavy colonization at the usual sites of infection indicates, but does not prove, that dissemination has occurred. The most reliable evidence of systemic candidiasis is biopsy demonstration of tissue invasion or recovery of yeast from fluid in a closed body cavity, such as cerebral spinal fluid, pleural or peritoneal fluid. Similarly, positive blood or urine or sputum cultures may indicate invasive disease or simply localized disease around indwelling devices, e.g., catheters or intravenous lines.

Mucocutaneous infections may be treated with topical preparations of nystatin, amphotericin B, clotximazole, miconazole, haloprogin or gentian violet. Oropharyngeal or esophageal candidiasis can be treated with systemic agents such as ketoconazole or fluconazole. Chronic mucocutaneous candidiasis syndrome may respond to topical or systemic therapeutic agents such as amphotericin B or ketoconazole, but often relapses when medication is discontinued. Cystitis may be treated with amphotericin B bladder rinses, or a brief low-dose intravenous course of amphotericin B with or without oral flucytosine. Endocarditis is essentially incurable without valve replacement, accompanied by a 6 to 10 week course of amphotericin B and flucytosine. Even with therapy, however, complete cure of endocarditis is not always possible.

The mortality rate from systemic candidiasis is about 50%. Systemic candidiasis may be treated with fluconazole, a fungistatic agent, or amphotericin B, a fungicidal agent although systemic use of the latter is limited by its toxicity. Both drugs have substantial adverse reactions when used in combination with cyclosporine A, which itself can be nephrotoxic. The removal of precipitating factors such as intravenous lines or catheters is also important for controlling infection. Flucytosine therapy can be added to the amphotericin B therapy for treatment of systemic candidiasis, especially in patients that are not imnmunocompromised. In immunocompromised patients, however, these infections are problematic and resist effective treatment. Mortality with systemic candidiasis can be over 90% in such patients. Furthermore, chronic mucocutaneous candidiasis and candidal endocarditis often show evidence of disease after having been declared cured.

Infection of the cornea and conjunctiva, including keratoconjunctivitis, can result from infection by amoeba, viruses, fungi and bacteria. Debilitated patients can develop keratitis from fungi such as Candida or Fusarium which is often associated with corneal ulceration and can lead to scarring with severe visual loss.

Amiodarone

Amiodarone is a Class III antiarrhythnic drug (Amiodarone in Physicians GenRx, 1996, BeDell, et. al, eds., Mosby-Year Book, Inc., St. Louis, Mo.; Amiodarone in *Drug Information for the HealthCare Profession*, 1997, USP DI, Twinbrook Parkway, Md; pp. 80–83). It is administered orally in 200 mg tablets and is sold under the name Cordarone® in the United States and several other brand names outside the U.S. Amiodarone prolongs the repolarization phase of the cardiac action potential. Amiodarone has beneficial effects in the treatment of patients with ventricular arrhythnias after myocardial infarction. Amiodarone therapy for arrhythmia requires prolonged treatment on the order of months to years. However, amiodarone dosed for this use has several unwanted side-effects, including thyroid dysfunction, hepatitis, impaired vision, photosensitivity of the skin, and pneumonitis. Amiodarone therapy for arrhythmia requires prolonged treatment on the order of months to years.

In animals, amiodarone is effective in the prevention or suppression of experimentally induced arrhythmias. The antiarrhythmic effect of amiodarone may be due to at least two major properties: 1) a prolongation of the myocardial cell-action potential duration and refractory period; and 2) noncompetitive alpha- and beta-adrenergic inhibition. Amiodarone prolongs the duration of the action potential of all cardiac fibers while causing minimal reduction of dV/dt. The refractory period is prolonged in all cardiac tissues.

Following oral administration in man, aniodarone is slowly and variably absorbed. The bioavailability of amiodarone is approximately 50% but has varied between 35 and 65% in various studies. Maximum plasma concentrations are attained 3 to 7 hours after a single dose. Despite this, the onset of Amiodarone's antiarrhythmic effect may take several days to 1 to 3 weeks to occur, even when administered with a loading dose. Plasma concentrations with chronic dosing at 100 to 600 mg/day are approximately dose proportional, with a mean 0.5 mg/L increase for each 100 mg/day administered. However, considerable individual variability occurs.

Amiodarone has a very large but variable volume of distribution, averaging about 60 L/kg because of extensive accumulation in various sites, especially adipose tissue and highly perfused organs, such as the liver, lung, and spleen. One major metabolite of amiodarone, desethylamiodarone, has been identified in man; it accumulates to an even greater extent in almost all tissues. The pharmacological activity of this metabolite, however, is not known. During chronic treatment, the plasma ratio of metabolite to parent compound is approximately one. The main route of amiodarone elimination is via hepatic excretion into bile.

There may be significant adverse side effects with the use of amiodarone. These include neurotoxicity, photosensitivity, and pulmonary fibrosis or interstitial pneumonitis/alveolitis. Ataxia is the most common symptom, occurring in 20–40% of patients, especially during administration of loading doses. It may occur within 1 week to several months after initiation of therapy and may persist for more than a year after withdrawal. Photosensitivity may require ultraviolet-A sun-block, such as zinc or titanium oxide and protective clothing. Pulmonary fibrosis or interstitial pneumonitis/alveolitis is clinically significant in up to 10 to 15% of patients, but abnormal diffusion capacity occurs in a much higher percentage of patients, more frequently with doses of 400 mg/day and after several months of treatment. It is usually reversible after withdrawal of amiodarone but is fatal in about 10% of cases, especially when not diagnosed promptly.

Incidence of adverse side effects is generally related to dose and duration of therapy. Adverse side effects may occur even at therapeutic plasma amiodarone concentrations, but are more common at concentrations over 2.5 $\mu$g per ml and with continuous treatment for longer than 6 months.

Amiodarone has also been found to affect mammalian G protein activity by Hagelüken, et al., 1995, *Mol. Pharmacol.* 47: 234–240 who reported that amiodarone increased high affinity GTP hydrolysis with an EC50 of 7.5 $\mu$M and stimulated binding of guanosine-5$\mu$-O-(3-thio)triphosphate to, and incorporation of GTP azidoanilide into Gi protein subunits in HL-60 membranes. These authors also found that amiodarone increased the cytosolic $Ca^{2+}$ concentration in HL-60 cells in the presence but not in the absence of extracellular $Ca^{2+}$. In vitro, amiodarone activated the GTPase of reconstituted Gi/Go proteins and Gi2 with EC50 values of 20 $\mu$M and 50 $\mu$M, respectively. These authors concluded that amiodarone is a direct activator of Gi and Go proteins and that amiodarone activates nonselective cation channels in HL-60 cells via Gi proteins.

There continues to exist a need in the art for new products and methods for their use as antifungal agents. In particular, effective antifungal therapy for systemic mycoses is limited. Products and methods responsive to this need would ideally involve substantially non-toxic compounds available in large quantities. Ideal compounds would have a rapid effect and a broad spectrum of fungicidal or fungistatic activity against a variety of different fungal species when administered or applied as the sole antifungal agent. Ideal compounds would also be useful in combinative therapies with other antifungal agents, particularly where these activities would reduce the amount of antifungal agent required for therapeutic effectiveness, enhance the effect of such agents, or limit potential toxic responses and high cost of treatment. Particularly advantageous would be compounds that are orally available and active for administration of antifungal agents.

SUMMARY OF THE INVENTION

The present invention provides methods of treating a subject suffering from a fungal infection by administering a therapeutically effective amount of an amiodarone compound. This is based on the surprising discovery that amiodarone has antifungal/fungicidal effects. An amiodarone compound may be administered alone or in conjunction with known antifungal agents. When made the subject adjunctive therapy, the administration of an amiodarone compound may reduce the amount of amiodarone compound and/or antifungal agent needed for effective therapy, thus limiting potential toxic response and/or high cost of treatment. Administration of an amiodarone compound may also enhance or accelerate the effect of such agents.

In addition, the invention provides a method of killing or inhibiting growth of fungi comprising contacting the fungi with an arniodarone compound. This method can be practiced in vivo or in a variety of in vitro uses such as to decontaminate fluids and surfaces and to sterilize surgical and other medical equipment and implantable devices, including prosthetic joints and indwelling invasive devices.

A further aspect of the invention involves use of an amiodarone compound for the manufacture of a medicament for treatment of fungal infection. The medicament may include, in addition to an amiodarone compound, other chemotherapeutic agents such as antifungal agents.

The invention further provides methods of prophylactically or therapeutically treating an immunocompromised subject comprising the step of administering to said subject an amount of amiodarone compound effective to kill or inhibit replication of fungi.

Thus, an agent that demonstrates broad antifungal activity has been identified. Detailed analysis has been carried out with the opportunistic pathogen, *Cryptococcus neoformans*. The agent, amiodarone, is a drug that is already in clinical use as an antiarrythmic drug. Amiodarone has fungicidal activity against Cryptococcus when used in the low micromolar concentration range. This new use of amiodarone provides an important new addition to the limited arsenal of antifungal agents that can be used for medicinal and agrochemical purposes.

Numerous additional aspects and advantages of the invention will become apparent to those skilled the art upon considering the following detailed description of the invention, which describes the presently preferred embodiments thereof.

BRIEF DESCRIPTION OF THE DRAWINGS

FIGS. 1 and 2 show results of growth of JEC21 cells, at 30° C. and 37° C., respectively, in the presence or absence of amiodarone; FIG. 3 shows results of growth and doubling time of JEC21 cells at 30° C. (A) and 37° C. (B) in the presence or absence of amiodarone; FIG. 5 shows results of growth of JEC21 cells in the presence of amiodarone, fluconazole or both.

FIG. 6 shows results of growth of JEC20 cells in the presence of aluminum fluoride.

DETAILED DESCRIPTION OF THE INVENTION

Figure 1B:
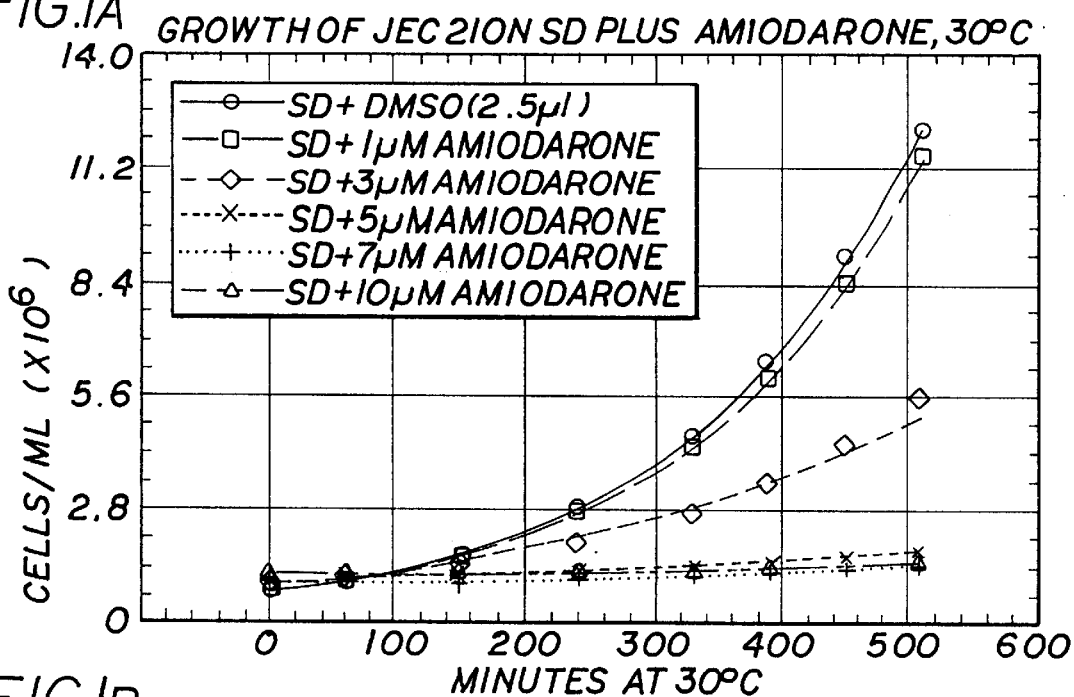

The present invention relates to the surprising discovery that an amiodarone compound can be administered to treat subjects suffering from fungal infection, and provides methods of treating such infections. Unexpectedly, amiodarone was demonstrated to have antifungal activities, including fungicidal activity. Tests for antifungal activity of an amiodarone compound according to the invention may be performed in in vitro killing assays and/or in in vivo models of fungal infection, as measured, for example, by improved survival or reduction of colony-forming units in circulation after fungal challenge. A variety of fungal infections, including infections caused by Cryptococcus, such as cryptococcal meningitis, infections caused by Aspergillus, and infections caused by Candida species, including mucocutaneous and systemic candidiasis, may be treated according to the invention. Treatment, as used herein, encompasses both prophylactic and therapeutic treatment. Subject, as used herein, is meant to refer to higher organisms, including animals (e.g., humans; companion animals such as dogs; livestock such as horses, cows and pigs; poultry; insects; fish; avian species) and plants. An amiodarone compound, as used herein, is meant to refer to the agent designated amiodarone and specifically includes the salt formulation aniodarone hydrochloride {(2-Butyl-3-benzofuranyl) [4-[2-(diethylamino)-ethoxyl]-3,5-diiodophenyl] ketone, hydrochloride} known and marketed in the U.S. as Cordarone®. An amiodarone compound, as used herein, also may include an amiodarone derivative that has antifungal activity according to the invention. Amiodarone derivatives for treatment of cardiac arrhythmias have been described (see, e.g., U.S. Pat. No. 5,849,788).

Pharmaceutical compositions useful according to the invention comprise an amiodarone compound with antifungal properties and a pharmaceutically acceptable diluent, adjuvant or carrier and are administered topically, intravenously, orally or as an aerosol.

In vitro methods of the invention permit killing or inhibiting replication of fungi through contacting the fungi with an amiodarone compound or a pharmaceutical composition containing the same. Fungal infection treatment methods of the invention comprise administering to a subject suffering from a fungal infection a therapeutically effective amount of an amiodarone compound according to the invention and such treatment methods are applicable to fungal infection, including, for example, infection by Cryptococcus, Aspergillus or Candida (especially, *C. albicans, C. glabrata, C. krusei, C. lusitaniae, C. parapsilosis* and *C. tropicalis*) species and others as described herein. Therapeutically effective amounts include amounts effective to inhibit replication of or kill fungi.

Administration of such amiodarone compounds may be especially beneficial in immunocompromised patients, including immuno suppressed and neutropenic patients, for example, patients undergoing chemotherapy, radiation therapy, or immunosupressive therapy, or patients with a dysfunctional immune system secondary to infection, such as HIV infection, or other causes. Topical administration of derivative compounds of the invention is also expected to be effective for treating a variety of fungal infections, including, for example, skin and eye infections, including those caused by dermatophytes.

Medicaments/pharmaceutical compositions useful according to the invention can include other antifungal agents including non-amiodarone agents or can be used in combinative therapeutic methods with other such agents.

An antifungal activity of an amiodarone compound in in vitro and/or in vivo methods/medicaments of the invention includes antifungal activity, for example, against species of Candida, Aspergillus, Cryptococcus, Histoplasma, Coccidioides, Blastomyces, Basidiobolus, Conidiobolus, Rhizopus, Rhizomucor, Mucor, Absidia, Mortierella, Cunninghamella, Saksenaea, Fusarium, Trichophyton, Trichosporon, Microsporum, Epidermophyton, Scytalidium, Malassezia, Actinomyceees, Sporothrix and Penicillium.

An amiodarone derivative compound according to the invention may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of ointments, gels, salves, ophthahnic drops, ear drops, or irrigation fluids (for example, irrigation of wounds).

Those skilled in the art can readily optimize effective dosages and administration regimens for compositions comprising an amiodarone compound as determined by good medical practice and the clinical condition of the individual subject.

An amiodarone compound useful according to the invention may be administered in conjunction with other antifungal agents. These non-amiodarone antifungal agents may include azole derivatives such as the imidazoles and triazoles (e,g., ketoconazole, clotrimazole, miconazole, econazole, butoconazole, oxiconazole, sulconazole, terconazole, fluconazole and itraconazole); amphotericin B, nystatin and pimaricin; flucytosine (5-fluorocytosine); allylamines-thiocarbamates, such tolnaftate and naftifine; griseofulvin, haloprogin, undecylic acid, ciclopirox olamine, tolnaftate and terbinafine.

Concurrent administration of an amiodarone compound according to the invention with other (e.g., non-amiodarone) antifungal agents is expected to improve the therapeutic effectiveness of the antifungal agents. This may occur through reducing the concentration of antifungal agent required to eradicate or inhibit fungal growth, e.g., replication. Because the use of some agents is limited by their systemic toxicity or prohibitive cost, lowering the concentration of antifungal agent required for therapeutic effectiveness reduces toxicity and/or cost of treatment, and thus allows wider use of the agent, Concurrent administration of an ariodarone compound according to the invention and another antifungal agent may produce a more rapid or complete antifungal/fungicidal effect than could be achieved with either agent alone. Administration of an amiodarone compound according to the invention may reverse the resistance of fungi to antifungal agents. Administration of an amiodarone compound according to the invention may also convert a fungistatic agent into a fungicidal agent.

An advantage provided by the present invention is the ability to treat fungal infections, particularly fungal infections from Cryptococcus, Aspergillus, or Candida, that are presently considered incurable. Another advantage is the ability to treat fungi that have acquired resistance to known antifungal agents. A further advantage of concurrent administration of an amiodarone compound according to the invention with an antifungal agent having undesirable side effects, e.g., amphotericin B, is the ability to reduce the amount of antifungal agent needed for effective therapy. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

Concurrent administration, as used herein, includes administration of the agents together, simultaneously or before or after each other. An amiodarone compound according to the invention and antifungal agents may be administered by different routes. For example, the an amiodarone compound may be administered intravenously while the other antifungal agents are administered intramuscularly, intravenously, subcutaneously, orally or intraperitoneally. Alternatively, the amiodarone compound may be administered intraperitoneally while the other antifungal agents are administered intraperitoneally or intravenously, or the amiodarone compound may be administered in an aerosolized or nebulized form while the other antifungal agents are administered, e.g., intravenously. The amiodarone compound and antifungal agents may be both administered orally. The amiodarone compound and antifungal agents may be given sequentially in the same intravenous line, after an intermediate flush, or may be given in different intravenous lines. The amiodarone compound and antifungal agents may be administered simultaneously or sequentially, as long as they are given in a manner sufficient to allow both agents to achieve effective concentrations at the site of infection.

Concurrent administration of amiodarone compound and another antifungal agent is expected to provide more effective treatment of fungal infections. Concurrent administration of the two agents may provide greater therapeutic effects in vivo than either agent provides when administered singly. For example, concurrent administration may permit a reduction in the dosage of one or both agents with achievement of a similar therapeutic effect. Alternatively, the concurrent administration may produce a more rapid or complete fungicidal/fungistatic effect than could be achieved with either agent alone.

Therapeutic effectiveness is based on a successful clinical outcome, and does not require that the antifungal agent or agents kill 100% of the organisms involved in the infection. Success depends on achieving a level of antifungal activity at the site of infection that is sufficient to inhibit the fungi in a manner that tips the balance in favor of the host. When host defenses are maximally effective, the antifungal effect required may be minimal. Reducing organism load by even one log (a factor of 10) may permit the host's own defenses to control the infection. In addition, augmenting an early fungicidal/fungistatic effect can be more important than long-term fungicidal/fungistatic effect. These early events are a significant and critical part of therapeutic success, because they allow time for host defense mechanisms to activate.

The invention provides a method of killing or inhibiting growth of fungi comprising contacting the fungi with an amidarone compound according to the invention. This method can be practiced in vivo or in a variety of in vitro uses such as in agricultural uses or food preparations or to decontaminate fluids and surfaces or to sterilize surgical and other medical equipment and implantable devices, including prosthetic joints. These methods can also be used for in situ sterilization of indwelling invasive devices such as intravenous lines and catheters, which are often foci of infection.

A further aspect of the invention involves use of an amiodarone compound according to the invention for the manufacture of a medicament for treatment of fungal infection. The medicament may include, in addition to such amiodarone compound, according to the invention, other chemotherapeutic agents such as antifungal agents. The medicament can optionally comprise a pharmaceutically acceptable diluent, adjuvant or carrier.

The administration of antifungal amiodarone compounds is suitably accomplished with a pharmaceutical composition comprising an amiodarone compound and a pharmaceutically acceptable diluent, adjuvant, or carrier. The amiodarone compound may be administered without or in conjunction with known surfactants, other chemotherapeutic agents or additional known antifungal agents.

EXAMPLE 1

Amiodarone Effects on Crytococcal Growth

Figure 1A:
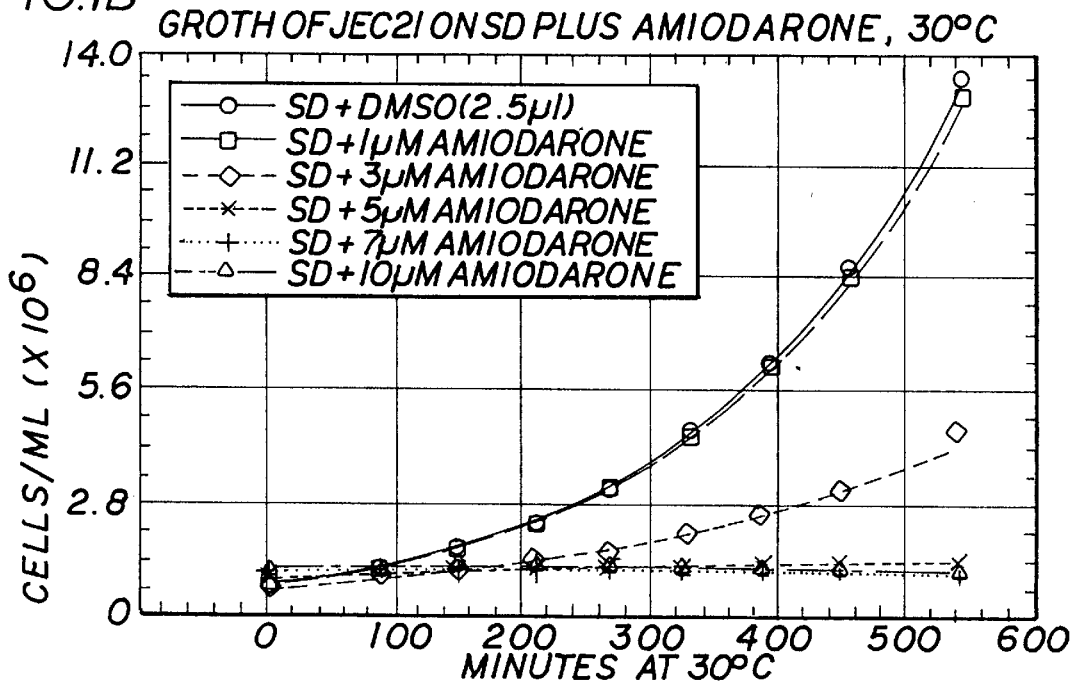

The effects of arniodarone treatment was tested on the growth and viability of C. neoformans in liquid cultures. Cryptococcal strain JEC21 was grown overnight in synthetic minimal medium (SD) at 30° C. to mid-exponential phase. Aliquots of the overnight culture were used to inoculate fresh media containing various concentrations of amiodarone (from Sigma or ICN). Amiodarone was diluted from a concentrated stock solution in DMSO. Control cells received DMSO only. The fresh media were inoculated at about 5–25×10$^5$ cells/ml and incubated at 30° C. or 37° C. The cell densities were monitored with a Klett-Somersome colorimeter. Typically, the cell density was monitored for about 10 hours. The results of these dose-response experiments are shown in FIGS. 1 and 2. The averages of these dose-response curves were plotted as bar graphs (FIG. 3) showing the fraction of the doubling time in the absence of amiodarone divided by the doubling time in the presence of a given concentration of amiodarone. This generates a value less than 1.0 that decreases as the amiodarone concentration increases. At amiodarone concentrations of 3–5 μM, at 30° C., cell density increased at a significantly lower rate than did the no-amiodarone control, while at 37° C., there was a significant reduction in the rate of cell increase at 1–3 μM amiodarone. At amiodarone concentrations around 7–10 μM, at 30° C., the cell density did not increase above the inoculation density, while at 37° C., there was no increase in cell density at 5 μM amiodarone or above.

Figure 4A:
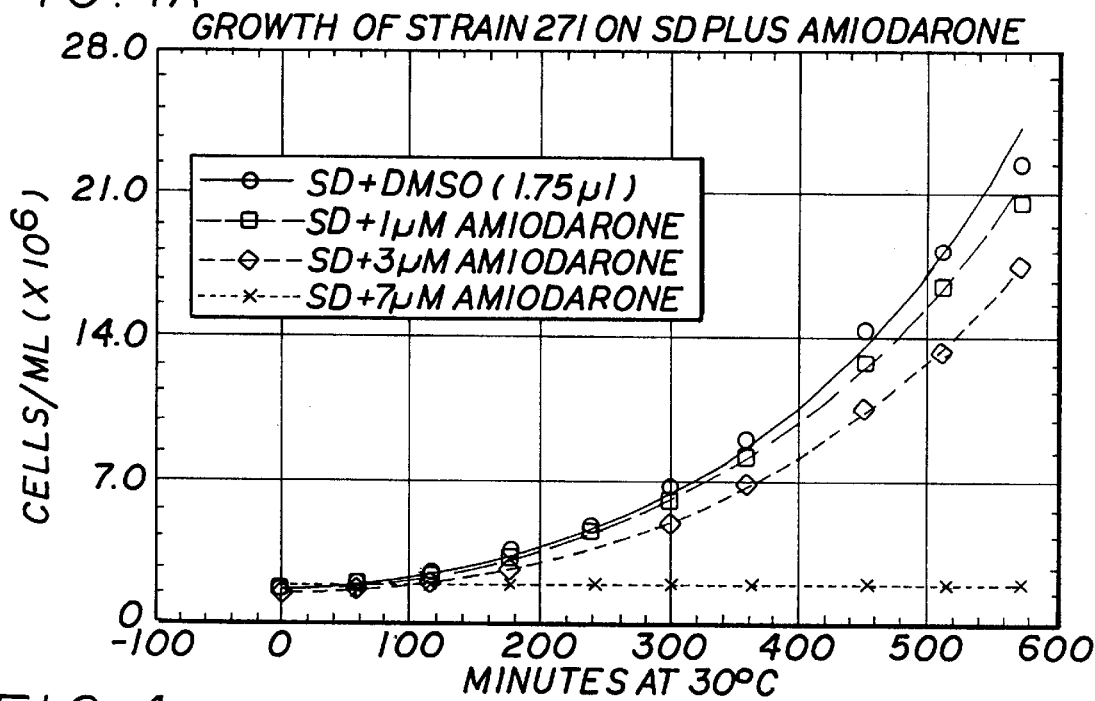
FIG. 4 shows results of grown of strain 271 cells (A) and JD9 (B) in the presence or absence of amiodarone.
Figure 4B:
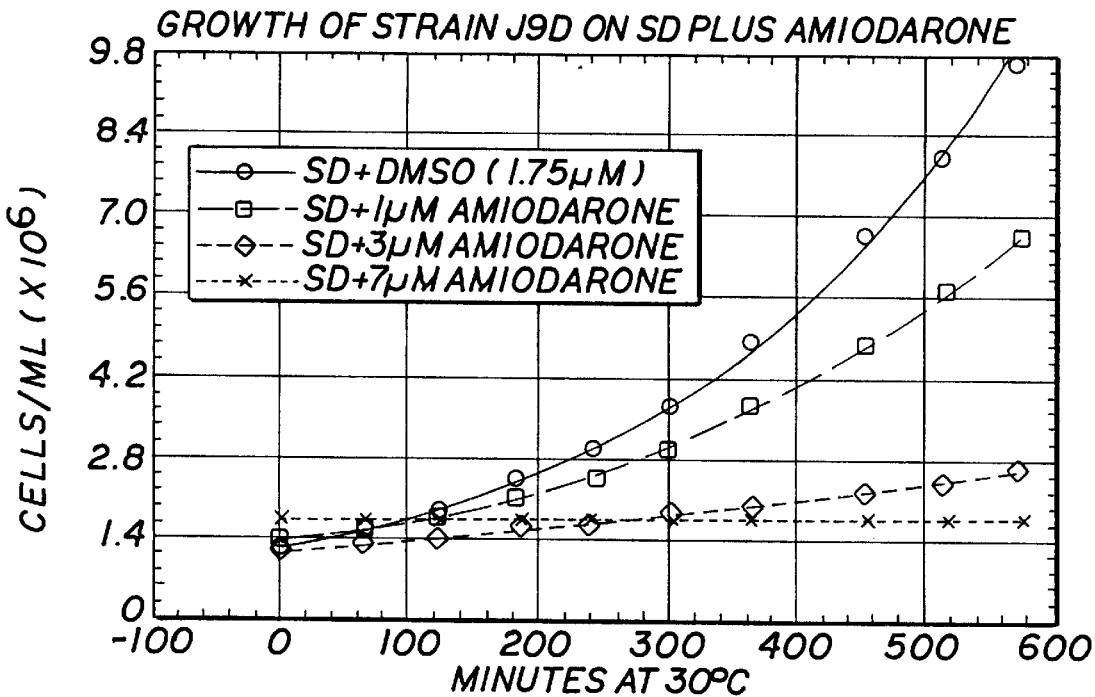

Experiments were performed to test whether the effects of amiodarone on growth and viability were specific to strain JEC21 (a genetically characterized lab strain) or more broadly applicable. Dose-responses of two other *C. neoformans* strains, 271 and J9D, which are clinical isolates were tested (FIG. 4). Both of these strains showed similar growth curves in response to 1, 3, and 7 μM amiodarone as JEC21; strain 271 was slightly less sensitive than JEC21, while J9D was more sensitive to growth inhibition by amiodarone. However, with both strains, as with JEC21, no increases in cell density occurred when cells were treated with 7 μM amiodarone.

Additional experiments were performed confirming the effect of amiodarone on the growth of *C. neoformans* cells as measured in liquid cultures. In these experiments, JEC21 cells were grown overnight in SD minimal medium (30° C.) to mid/late exponential phase. At zero time, aliquots were transferred into fresh SD medium containing either amiodarone or DMSO as a control. Cell densities (which began at about 1–2×10$^6$ cells/ml) were measured over an approximately 10 hour period and the results plotted to produce growth curves. Dose-response curves were constructed for cells treated with varying concentrations (1–10 μM) of amiodarone. Each curve was the mean of 4 independent experiments and rates of increase were used to determine the generation times shown in Table 1. During this period, the control cells (which received only DMSO) increased in density about 10 fold to around 1.5×10$^7$ cells/ml and grew at a rate of 171.3 mil/generation (Table 1). Addition of 1 μM amiodarone did not alter the generation time of the JEC21 cells, while addition of 3 μM amiodarone doubled the length of the generation time (to 273 minutes/generation). Addition of amiodarone at 5 μM or above prevented virtually any increase in cell density during this period. Growth of Cryptococcus at high temperature is an important virulence factor for this fungi, thus the effect of amiodarone was examined on the growth of cells at 37° C. While no effect on growth was seen in cultures with 1 μM aniodarone, cultures containing 3 μM amiodarone displayed growth rates of 432 minutes/generation, about 58% slower than at 30° C., showing an exacerbating effect of higher temperature. As with 30° C., no increase in cell density occurred in cultures treated with amiodarone at 5 μM or above. Thus, amiodarone treatment dramatically inhibits cryptococcal proliferation.

TABLE 1

Effect of amiodarone on fungal growth*

| *Cryptococcus neoformans* Strains | | | *Saccharomyces cerevisiae* | | *Aspergillus fumigatus* | |
|---|---|---|---|---|---|---|
| Amiodarone concentration | JEC21 | 271 | Amiodarone concentration | BC159 | Amiodarone concentration | B-5233 |
| | Doubling Times | | | Doubling Times | | Cell Weight (mg) |
| 0 μM | 136 (3.5) | 189 (15.1) | 0 μM | 196 (9.6) | 0 μM | 4.1 (0.6) |
| 1 μM | 139 (3.0) | 188 (13.0) | 5 μM | 258 (15.4) | 5 μM | 1.4 (0.4) |
| 3 μM | 273 (50.9) | 203 (21.9) | 10 μM | 983 (125.9) | 15 μM | 0.4 (0.1) |
| 5 μM | NG^ | 1983 (1488) | 15 μM | NG^ | 50 μM | 0.0 (0.0) |
| 7 μM | NG^ | NG^ | | | | |

*All cells were grown in liquid SD medium. Growth of the Cryptococcus and Saccharomyces strains was measured in a Klett-Summerson colorimeter. Doubling times are in minutes/generation. Growth of the Aspergillus strain was determined by measuring the dry weight (in mg) of cultures after two days growth, as described in Materials and Methods. All values are the means of 3–4 independent experiments with the standard errors shown in parentheses.
^NG: no growth occurred during 24 hours after drug exposure.

Additional experiments also confirmed the effect of amiodarone treatment on the growth of the clinical isolate strain 271 (Table 1). Amiodarone very effectively inhibited the growth of the clinical isolate; for example, as shown in Table 1, 271 growth was only slightly effected by the presence of 3 μM amiodarone but was largely inhibited by 5 μM and, like JEC21 did not grow in the presence of 7 μM. Moreover, as shown above in FIG. 4B, growth of another clinical strain (J9D) was more severely inhibited by amiodarone than was JEC21. Thus, the inhibitory effect of amiodarone was demonstrated with a variety of Cryptococcal strains.

Amiodarone treatment was found to inhibit the growth of several other fungi, including *Fusarium oxysporum, Magnaporthe grisea, Aspergillus nidulans, Aspergillius fumigatus*, and *Candida albicans*, and *Saccharomyces cerevisiae*, (see, e.g., Table 1). Inhibition of growth of these fungi required amiodarone in the low to moderate micromolar range. Thus, amiodarone blocked the proliferation of heterobasidiomycetes (e.g., Cryptococcus), ascomycetes (e.g., Saccharomyces) and hyphomycetes (e.g., Aspergillus). Therefore, amiodarone should have a wide spectrum of antifungal activity.

EXAMPLE 2

Amiodarone Displays Synergistic Effects with Other Antifungals

Fluconazole is the first of a new subclass of synthetic triazole antifungal agent. Fluconazole is used to treat and to prevent a variety of fungal infections. People living with HIV infection use fluconazole most often to treat candidiasis in the mouth (thrush), throat (esophageal candidiasis), or vagina (yeast infection). Fluconazole is also approved for the treatment of cryptococcal infections, including meningitis. Fluconazole is used to treat fungal infections and to prevent them from coming back. Fluconazole acts by inhibiting ergosterol biosynthesis at the C-14 demethylation step. It exhibits a broad antifungal activity, including yeasts and filamentous fungi.

The growth of Cryptococcal cells (JEC21) was examined in the presence of concentrations of amiodarone and fluconazole that, by themselves, did not inhibit growth. When the drugs were combined at these sub-inhibitory concentrations, they produced a significant decrease in the growth rate of cells (FIG. 5). Thus, there is a synergistic effect that suggests that a combinatorial treatment with these two drugs should be beneficial and should have increased antifungal potency and efficacy over that seen with either drug when used alone.

EXAMPLE 3

Fungicidal Effect

Experiments were performed to test whether the lack of increase in cell density was a result of a fungistatic or fungicidal effect. Cryptococcal cells (JEC21) were treated with 10 $\mu$M amiodarone, at 30° C., and samples were taken at various times after treatment and plated on SD agar medium (incubated at 30° C.) to test for viable cells (Table 2). After one hour of exposure, only 7.2% of the cells remained viable and by three hours of exposure, 0.3% of the cells were viable. By 25 hours of exposure less than 1 cell out of $10^6$ cells were viable. Similar experiments with cells treated at 37° C. showed that cells were more sensitive to amiodarone than at 30° C., with a decrease in viability for cells treated with 7 $\mu$M amiodarone at 37° C. approximately equal to that for cells treated with 10 $\mu$M at 30° C. The results shown in Table 2 demonstrate a potent fungicidal effect of amiodarone.

TABLE 2

Viability of *C. neoformans* after amiodarone exposure

| Exposure Time (hours)* | Temp. (° C.) | % Viable Cells Expt. 1 | % Viable Cells 4 Expt. Summary | (Std. error)** |
|---|---|---|---|---|
| 0 | 30 | 100 | 100 | (NA) |
| 1 | 30 | 12.2 | 10.0 | (2.1) |
| 3 | 30 | 4.6 | 3.7 | (1.5) |
| 5 | 30 | 2.3 | 1.8 | (0.8) |
| 10 | 30 | 0.5 | 0.4 | (0.2) |
| 25 | 30 | 0.001 | 0.001 | (0.001) |
| 50 | 30 | 0.0 | 0.0 | (0.0) |
| 0 | 37 | 100 | | |
| 24 | 37 | 0.2 | | |
| 48 | 37 | 0.1 | | |
| 72 | 37 | 0.0001 | | |

*C. neoformans* was grown in SD medium at the indicated temperatures. At 0 hours, cells were treated with 10 $\mu$M or 7 $\mu$M amiodarone for cultures grown at 30° C. or 37° C., respectively. At the indicated times, the cultures were sampled for colony-forming units (i.e., viable cells) by plating on SD-agar medium. Colonies were counted after several days growth at 30° C.. Percent (%) viable cells were determined versus the 0 hours time point.
**Summary of data of 4 experiments, including Expt. 1.

In summary, an agent has been identified, amiodarone, that has broad antifungal activity against both yeast and filamentous fungi. As an example, amiodarone is particularly effective against *C. neoformans* cells, inhibiting growth when used in the very low micromolar range. Importantly, amiodarone demonstrates fungicidal effects against cryptococcal cells. An amiodarone compound should also be useful in treating a variety of fungal infections (e.g., those caused by Pneumocystis, Candida, or Histoplasma, both systemic and topical. The rapid fungicidal effects of amiodarone suggest that short treatment periods may be possible, thereby limiting any potentially deleterious side effects. Finally, amiodarone acts synergistically with other antifungals, such as fluconazole to inhibit cryptoccal growth. This raises the potential for using amiodarone in conjunction with other antifungals to provide a more effective treatment regime, potentially at lower doses, than is possible by treatment with single antifungal agents. Since amiodarone is already an FDA approved drug that is currently in clinical use, it should dramatically reduce the time needed to have this agent approved for use an antifungal drug. The use of an amiodarone compound should also be effective in treating fungi in agricultural settings. Species of Fusarium and Magnaporthe are also growth inhibited by amiodarone demonstrating effectiveness against a wide range of fungi, including those of agricultural importance.

EXAMPLE 4

Effect of Cations on Sensitivity to Amiodarone

It has been suggested that amiodarone affects ion channels in mammalian cells. Experiments were performed with fungal cells to test whether addition of cations to the growth medium would affect the growth inhibition caused by amiodarone. Cryptococcal cells (JEC21) growing in SD minimal medium were treated with 4 $\mu$M amiodarone to cause a marked decrease (but not total inhibition) in their growth rate. In parallel cultures, cells were simultaneously given either CaCl12 (10 mM), MgCl2 (10 mM), or NaCl (20 mM). Control cultures received the salt additions without amiodarone. The growth rates of each culture were followed over several hours and generation times were determined and are shown in Table 3. 4 $\mu$M amiodarone treatment caused a lengthening of the generation time to 314.1 minutes compared to the 171.3 minutes for the DMSO control. The addition of $CaCl_2$ was very effective in antagonizing the amiodarone-induced inhibition, allowing a generation time (190.5 minutes) similar to that of the control, while treatment with $MgCl_2$ weakly suppressed growth inhibition (generation time of 216.7 min.). In contrast, addition of NaCl had only a minor effect on the generation time (281.5 min.) compared to the amiodarone-only treatment. The addition of the salts by themselves did not affect the generation times (Table 3). Thus, addition of divalent cations, in particular calcium, to the growth medium antagonized the growth inhibitory effects caused by amiodarone, suggesting that amiodarone affects cation metabolism.

TABLE 3

Effect of cations on the growth inhibition caused by amiodarone*

|  | DMSO only | Amiodarone only | Amiodarone + CaCl$_2$ | Amiodarone + MgCl$_2$ | Amiodarone + NaCl | CaCl$_2$ only | MgCl$_2$ only | NaCl only |
|---|---|---|---|---|---|---|---|---|
| Mean | 171.3 | 314.1 | 190.5 | 216.7 | 281.5 | 171.3 | 187.2 | 179.3 |
| Standard Error | (14.2) | (33.4) | (2.1) | (9.0) | (17.6) | (5.4) | (10.8) | (2.7) |

*Generation Times (minutes per generation) for JEC21 grown at 30° C. in SD medium supplimented as indicated. Concentrations were: Amiodarone, 4 μM; CaCl$_2$, 10 mM; MgCl$_2$, 10 mM; NaCl, 20 mM; DMSO, 0.4 μl/ml.

In additional experiments, a survey of *Saccharomyces cerevisiae* mutants was conducted. The entire genome of this yeast has been sequenced and more than 6000 genes tentatively identified. Analysis of these genes and their putative protein products has revealed homology to known genes and proteins. In particular, a number of genes have been identified whose encoded proteins are homologous to channel proteins (Nelissen, et al, 1997, *FEMS Microbiological Reviews* 21: 113–134). In these experiments, the effect of amiodarone was measured on the growth of numerous strains deleted for genes that are believed to encode cation-channel proteins. Strains were analyzed with deletions of 11 genes: YRJ106w, YNL321w, YBR086c, YBR131w, YDL206w, YIL048w, MID1, CCH1, PMC1, VCX1, and CSG2. Of these 11 strains, only those deleted for either YNL321w or YDL206w were less sensitive to amiodarone than their wild type parental strains, however, each strain was still inhibited by amiodarone. These two genes are related to each other and are thought to encode proteins with homology to Ca$^{+2}$:cation antiporters. Cells carrying multiple copies of one of these genes (YNL321w) were shown to display an increased sensitivity to growth inhibition by amiodarone. These cells were also shown to accumulate radiolabeled calcium more rapidly, consistent with this gene encoding a calcium antiporter.

The ability of high concentrations of calcium to protect cells from growth-inhibition by amiodarone suggested a defect in uptake or retension of calcium. Efflux of radiolabeled calcium was measured in the *S. cerevisiae* strain FY70. Cells were incubated in growth medium containing 9.5 μC/ml Ca-45 (as $^{45}$CaCl$_2$) for 1 hour to allow accumulation of labeled calcium. Cells were subsequently sampled, washed free of external labeled calcium and suspended in H$_2$O. A zero time sample was taken and then cells were treated with 20 μM amiodarone or DMSO and samples taken over time. All samples were filtered and washed with 5 mM nonradioactive CaCl$_2$ to remove any labeled calcium that may have effluxed from the cells. The remaining cell-associated radioactivity was determined by measuring cell filtrates in a scintillation counter. The cell-associated radioactivity was rather stable over time in control cells treated with DMSO, since nearly 90% of the radioactivity was retained in cells during the assay period.

In contrast, cells exposed to amiodarone rapidly lost up to 70% of the labeled calcium within about 1 minute of treatment. Cells treated with amiodarone reaccumulated some of the effluxed calcium during the course of the experiment. Efflux experiments were repeated in the presence of 10 μM gadolinium or lanthanum chlorides. The presence of either of these cations did not block efflux of radiolabeled calcium from cells treated with aniodarone but did block the reaccumulation, suggesting that cells are able to take up calcium in the presence of amiodarone. Therefore, the ability of cells to accumulate calcium after longer exposure to amiodarone was measured.

The uptake of radiolabeled calcium was measured in the *S. cerevisiae* strain FY70 in the presence of arniodarone. Exponentially growing cells were treated with either DMSO or amiodarone for 1 hour at which time 9.5 μC/ml Ca-45 was added and accumulation of the label measured over time. Calcium uptake in control cells pretreated only with DMSO was linear over the 1 hour period of the assay. Uptake of calcium in cells pretreated with 20 μM amiodarone was also linear but occurred at a 2–3 fold slower rate compared to control cells. Thus, amiodarone appears to promote efflux and results in reduced ability to accumulate calcium.

Numerous modifications and variations of the above-described invention are expected to occur to those of skill in the art. Accordingly, only such limitations as appear in the appended claims should be placed thereon.

What is claimed is:

1. A method of treating fungal infections comprising administering to a subject suffering from a fungal infection a therapeutically effective amount of amiodarone or a pharmaceutically acceptable salt thereof.

2. The method of claim 1 wherein the amiodarone is administered in the form of amiodarone hydrochloride.

3. The method of claim 1 wherein the fungal infection involves a fungal species selected from the group consisting of Cryptococcus, Aspergillus, and Candida species.

4. The method of claim 3 wherein the fungal species is *Cryptococcus neoformans*.

5. The method of claim 1 wherein the amiodarone or a pharmaceutically acceptable salt thereof is administered intravenously.

6. The method of claim 1 wherein the amiodarone is administered orally.

7. The method of claim 1 wherein the amiodarone is administered topically.

8. The method of claim 1 comprising the additional step of administering a non-amiodarone antifungal agent.

9. A method of killing or inhibiting replication of fungi comprising contacting the fungi with amiodarone.

10. The method of claim 9 wherein the amiodarone is in the form of amiodarone hydrochloride.

11. The method of claim 10 further comprising contacting the fungi with an antifungal agent.

* * * * *